United States Patent [19]

Henrick et al.

[11] 3,970,704

[45] July 20, 1976

[54] ALKOXY SUBSTITUTED ALIPHATIC DI-OLEFINIC HALIDES

[75] Inventors: Clive A. Henrick; John B. Siddall, both of Palo Alto, Calif.

[73] Assignee: Zoecon Corporation, Palo Alto, Calif.

[22] Filed: Mar. 21, 1975

[21] Appl. No.: 560,851

Related U.S. Application Data

[60] Division of Ser. No. 217,930, Jan. 14, 1972, Pat. No. 3,890,398, which is a continuation-in-part of Ser. No. 187,897, Oct. 8, 1971, Pat. No. 3,755,411, which is a continuation-in-part of Ser. No. 111,650, Feb. 1, 1971, Pat. No. 3,729,486, and a continuation-in-part of Ser. No. 111,702, Feb. 1, 1971, abandoned, and a continuation-in-part of Ser. No. 111,765, Feb. 1, 1971, abandoned, and a continuation-in-part of Ser. No. 111,766, Feb. 1, 1971, abandoned, and a continuation-in-part of Ser. No. 111,770, Feb. 1, 1971, abandoned, and a continuation-in-part of Ser. No. 115,725, Feb. 16, 1971, Pat. No. 3,706,733.

[52] U.S. Cl. ............................. 260/614 R; 260/410
[51] Int. Cl.$^2$ ..................... C07C 43/00; C07C 43/17
[58] Field of Search ................................ 260/614 R

[56] References Cited

UNITED STATES PATENTS 3,711,516 1/1973 Siddall .......................... 260/614 R

OTHER PUBLICATIONS

Slama et al., Proceeding of the National Academy of Sciences, vol. 54, (1965), 413.
Sarmiento et al., Sci. 179, pp. 1342–1343, Mar. 1973.

*Primary Examiner*—Howard T. Mars
*Attorney, Agent, or Firm*—Donald W. Erickson

[57] ABSTRACT

Aliphatic hydrocarbon tri-olefinic and substituted aliphatic di-olefinic halides, and derivatives thereof, intermediates therefor, syntheses thereof, and the control of insects.

9 Claims, No Drawings

ALKOXY SUBSTITUTED ALIPHATIC DI-OLEFINIC HALIDES

This is a division of U.S. Ser. No. 217,930, Jan. 14, 1972, U.S. Pat. No. 3,890,398, which is a continuation-in-part of U.S. Ser. No. 187,897, Oct. 8, 1971, U.S. Pat. No. 3,755,411, which is a continuation-in-part of U.S. Ser. Nos. 111,650, Feb. 1, 1971, U.S. Pat. No. 3,729,486, and U.S. Ser. No. 111,702, Feb. 1, 1971, abandoned, and U.S. Ser. No. 111,765, Feb. 1, 1971, abandoned, and U.S. Ser. No. 111,766, Feb. 1, 1971, abandoned, and U.S. Ser. No. 111,770, Feb. 1, 1971, abandoned, and U.S. Ser. No. 115,725, Feb. 16, 1971, U.S. Pat. No. 3,706,733.

This invention relates to novel aliphatic di-olefinic compounds, aliphatic tri-olefinic compounds, intermediates therefor, syntheses thereof, and the control of insects. More particularly, the novel di-olefinic compounds of the present invention are represented by the following formula:

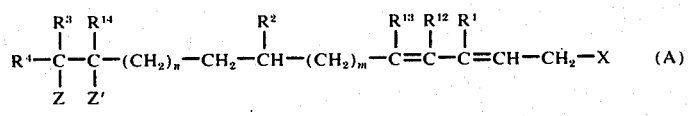

wherein,
X is bromo, chloro, fluoro or iodo;
Z is bromo, chloro, fluoro or the group —OR in which R is hydrogen, carboxylic acyl, lower alkyl, cycloalkyl, aralkyl or aryl;
Z' is hydrogen, bromo, chloro or fluoro;
each of $m$ and $n$ is zero or the positive integer one, two or three;
each of $R^1$ and $R^2$ is lower alkyl;
$R^4$ is alkyl; and
each of $R^3$, $R^{12}$, $R^{13}$ and $R^{14}$ is hydrogen or lower alkyl.

The compounds of formula A are useful for the control of insects. The utility of these compounds as insect control agents is believed to be attributable to their juvenile hormone activity. They are preferably applied to the immature insect, namely — during the embryo, larvae or pupae stage in view of their effect on metamorphosis and otherwise cause abnormal development leading to death or inability to reproduce. These compounds are effective control agents for Hemipteran, such as Lygaeidae, Miridae and Pyrrhocoridae; Lepidopteran, such as Pyralidae, Noctuidae and Gelechiidae; Coleopteran, such as Tenebrionidae, Crysomelidae and Dermestidae; Dipteran, such as mosquitos, flies; Homopteran, such as aphids; and other insects. The compounds can be applied at low dosage levels of the order of 0.001 μg. to 25.0 μg. per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of the compounds of formula A. Generally, a concentration of less than 25% of the active compound is employed. The formulations can include insect attractants, emulsifying agents or wetting agents to assist in the application and effectiveness of the active ingredient. In the application of the compounds, there is generally employed a mixture of the C-2,3 trans and cis isomers.

In the description hereinafter, each R-$R^4$, $R^{12}$-$R^{14}$, X, Z, Z', $m$ and $n$ is as defined hereinabove, unless otherwise specified.

In another embodiment of the present invention, there is provided compounds of the following formula B which are useful for the control of insects in the same manner as the diolefinic compounds of formula A and which also serve as precursors for the preparation of the compounds of formula A.

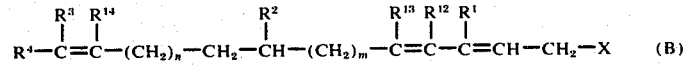

The allylic halides of formula A and B can be prepared from the respective allylic alcohol precursor of formula C and C' by halogenation:

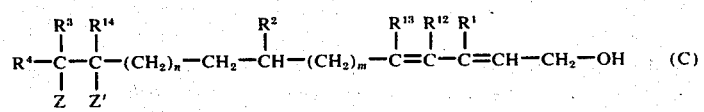

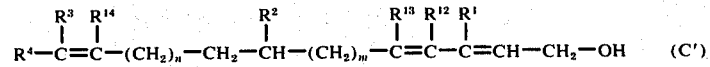

Suitable halogenation methods include the reaction of the allylic alcohol with a halogenation agent, such as a phosphorus trihalide or phosphorus pentahalide in an organic solvent inert to the reaction. Other suitable procedures include conversion of the allylic alcohol into the respective tosylate or mesylate followed by treatment with an alkali halide, such as lithium bromide, lithium iodide, lithium chloride, sodium iodide, sodium bromide, and the like, to prepare the respective halide. The fluorides can be prepared by reaction of an iodide or bromide with silver fluoride.

The allylic alcohols can be prepared by the reduction of an α,β-unsaturated acid or ester of formula B' using lithium aluminum hydride and the like, in an organic solvent inert to the reaction. The acids and esters of formula B', as well as the tri-unsaturated acids and esters, can be prepared as described, for example, in application Ser. No. 187,897, filed Oct. 8, 1971, the entire disclosure of which is incorporated by reference.

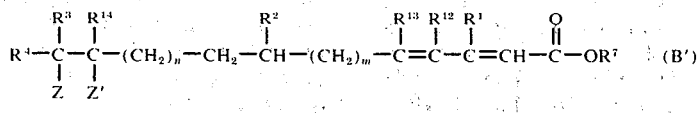

wherein R⁷ is hydrogen or lower alkyl.

The allylic bromides, chlorides, and iodides of formulas A and B are useful also as intermediates for the preparation of primary, secondary and tertiary amines which, in turn, are useful for the control of insects as described in application Ser. No. 187,897 and application Ser. No. 217,297, filed on or about Jan. 10, 1972 now U.S. Pat. No. 3,839,452.

The compounds of formula A wherein Z' is hydrogen and Z is halo can be prepared by treating a compound of formula B with hydrogen halide in an organic solvent such as carbon tetrachloride or other halogenated hydrocarbon solvents of low dielectric constant. The compounds of formula A wherein Z' is halo can be prepared by treating a compound of formula R with bromine, chlorine or fluorine in a halogenated hydrocarbon solvent.

The compounds of formula A wherein Z' is hydrogen and Z is the group —OR in which R is hydrogen can be prepared by the addition of water to the terminal olefinic bond of a compound of formula B using a mercuric salt followed by reduction of the oxymercurial intermidiate in situ. Suitable mercuric salts include mercuric acetate, mercuric nitrate, mercuric trifluoroacetate, mercuric acylates and mercuric halides. Suitable reducing agents include the borohydrides, hydrazine and sodium amalgam. See Brown and Rei, *J. Am. Chem. Soc.* 91, 5646 (1969); Brown et al., *J. Am. Chem. Soc.* 89, 1522 and 1524 (1967); and Wakabayashi, *J. Med. Chem.* 12, 191 (January, 1969). By conducting the reaction in the presence of an alcohol (R—OH) such as methanol, ethanol, isopropyl alcohol, benzyl alcohol, cyclopentanol, and the like, the corresponding ether is prepared. The compounds of formula A wherein Z is —OR in which R is carboxylic acyl and Z' is hydrogen can be prepared from a compound of formula A wherein Z is —OH and Z' is hydrogen by reaction with a carboxylic acid chloride or bromide or carboxylic acid anhydride in pyridine or by treatment with a carboxylic acid anhydride in the presence of sodium acetate. The reaction is generally conducted at about room temperature to reflux temperature for about one to fourty-eight hours, shorter reaction time being favored by temperatures above room temperature.

The term "cycloalkyl", as used herein, refers to a cyclic alkyl group of four to eight carbon atoms. The term "aralkyl" refers to a monovalent hydrocarbon group in which an aryl group is substituted for a hydrogen atom of an alkyl group, such as benzyl, xylyl, mesityl, phenylethyl, methylbenzyl, naphthylmethyl and naphthylethyl containing up to twelve carbon atoms. The term "aryl", as used herein, refers to an aromatic group of up to twelve carbon atoms. Typical aromatic groups include phenyl, naphthyl, lower alkylphenyl such as methylphenyl, ethylphenyl, t-butylphenyl and isopropylphenyl, lower alkylthiophenyl such as methylthiophenyl, ethylthiophenyl and isopropylthiophenyl, lower alkoxyphenyl such as methoxyphenyl and ethoxyphenyl, halophenyl such as chlorophenyl, bromophenyl, iodophenyl and fluorophenyl, nitrophenyl, and lower alkenylphenyl such as vinylphenyl and allylphenyl. In the case of substituted phenyl, the substituent such as lower alkyl, lower alkylthio, lower alkoxy, halo, nitro, lower alkenyl, and cyano, can be in one or more positions of the phenyl ring, usually in the para position.

The term "carboxylic acyl", as used herein, refers to the acyl group of a carboxylic acid, anhydride or halide. The acyl group is determined by the particular carboxylic acid halide or carboxylic acid anhydride employed in the esterification. Although no upper limitation need be placed on the number of carbon atoms contained in the acyl group within the scope of the present invention, generally it contains from one to 18 carbon atoms. Typical esters of the present invention include formate, acetate, propionate, enanthate, benzoate, trimethylacetate, trichloroacetate, trifluoroacetate, t-butylacetate, phenoxyacetate, cyclopentylpropionate, aminoacetate, β-chloropropionate, adamantoate, octadec-9-enoate, dichloroacetate, butyrate, pentanoate, hexanoate, phenylacetate, p-methylbenzoate, β-phenylpropionate, 3,4-dimethylbenzoate, p-isopropylbenzoate, cyclohexylacetate, stearate, methacrylate, p-chloromethylbenzoate, p-methoxybenzoate and p-nitrobenzoate.

The term "alkyl" refers to a branched or straight chain, saturated aliphatic hydrocarbon of one to twelve carbon atoms. The term "lower alkyl" refers to an alkyl group having a chain length of one to six carbon atoms.

The presence of an olefinic bond at position C-2 and C-4 of the compounds of formula A give rise to four isomers, each of which is embraced by the present invention. The presence of three olefinic bonds in compounds of formula B give rise to eight isomers, each of which is embraced by the present invention. As mentioned above, a mixture of isomers is suitably employed for the control of insects such as a mixture containing the trans (2), trans (4) isomer and the cis (2), trans (4) isomer. The conditions of the syntheses described herein and the reactants can be selected so as to favor formation of one isomer such as the all trans isomer over the formation of other isomers. The selection of appropriate conditions and reactants to favor formation of one isomer over another will be apparent to those of ordinary skill in the art giving due consideration to the specific examples hereinafter. See also Pattenden and Weedon, supra and /Corey et al., supra. In the specific examples hereinafter when isomerism is not specified, it is understood to include a mixture of isomers which, if desired, can be separated using known separation methods. Hereafter, when only one designation of configuration is given, the designation refers to position C-2,3 and the configuration is taken to be trans at position C-4,5 when not otherwise specified. The use of "trans/cis" and "cis/trans" is with reference to position C-2,3 and indicates a mixture of isomers.

The following examples are provided to illustrate the practice of the present invention. Temperature is given in degrees Centigrade.

EXAMPLE 1

To a mixture of one g. of 3,7-dimethyloct-6-en-1-al 1.5 g. of phosphonate (II; R' is ethyl, $R^1$ is methyl, $R^6$ is ethoxy, $R^{12}$ is hydrogen) and 50 ml. of dimethylformamide, under nitrogen, is slowly added sodium ethoxide (prepared from 200 mg. of sodium and 12 ml. of ethanol). The mixture is allowed to stand at room temperature for one hour and then is worked up with ether. The ethereal extracts are dried, concentrated and then chromatographed on silica plates eluting with hexane/ether to yield ethyl 3,7,11-trimethyldodeca-2,4,10-trienoate which is predominantly trans at position C-2,3 and C-4,5.

By using diethyl 3-methoxycarbonyl-2-methylprop-2-enyl phosphonate and sodium methoxide, there is prepared methyl 3,7,11-trimethyldodeca 2,4,10-trienoate.

EXAMPLE 2

The process of Example 1 is repeated using each of the aldehydes under column I as the starting material to yield the respective ester under column II

I 3,7-dimethylnon-6en-1al
3-ethyl-7-methylnon-6-en-1-al
3,7-diethylnon-6-en-1-al
4,8-dimethylnon-7-en-1-al
3,6-dimethylhept-5-en-1-al
3,6-dimethyloct-5-en-1-al
2,6-dimethylhept-5-en-1-al

II ethyl 3,7,11-trimethyltrideca-2,4,10-trienoate
ethyl 3,11-dimethyl-7-ethyltrideca-2,4,10-trienoate
ethyl 7,11-diethyl-3-methyltrideca 2,4,10-trienoate
ethyl 3,8,12-triemthyltrideca-2,4,11-trienoate
ethyl 3,7,10-trimethylundeca-2,4,9-trienoate
ethyl 3,7,10-trimethyldodeca-2,4,9-trienoate
ethyl 3,6,10-trimethylundeca-2,4,9-trienoate

EXAMPLE 3

A mixture of 1 g. of trans/cis methyl 3,7,11-trimethyldodeca-2,4,10-trienoate, 60 ml. of methanol, 0.5 g. of potassium hydroxide and 6 ml. of water is heated at reflux for about 8 hours. The mixture is then diluted with water, neutralized and extracted with ether. The organic phase is washed with water, dried over sodium sulfate and evaporated to yield trans/cis 3,7,11-trimethyldodeca-2,4,10-trienoic acid.

Using the foregoing procedure, the other esters of Example 2 are hydrolyzed to produce the respective free acids under column III.

III 3,7,11-trimethyltrideca-2,4,10-trienoic acid
3,11-dimethyl-7-ethyltrideca-2,4,10-trienoic acid
7,11-diethyl-3-methyltrideca-2,4,10-trienoic acid
3,8,12-trimethyltrideca-2,4,11-trienoic acid
3,7,10-trimethylundeca-2,4,9-trienoic acid
3,7,10-trimethyldodeca-2,4,9-trienoic acid
3,6,10-trimethylundeca-2,4,9-trienoic acid

EXAMPLE 4

One gram of thionyl chloride is added with stirring at room temperature to 0.5 g. of trans/cis 3,7,11-trimethyldodeca-2,4,10-tricnoic -trienoic and the mixture heated at about 50° for 10 minutes. Excess thionyl chloride is removed by evaporation and then t-butyl alcohol (about 2 equivalents) is added and the mixture heated at about 50° for about 5 minutes to yield t-butyl 3,7,11-trimethyldodeca-2,4,10-trienoate (trans/cis).

By using other alcohols in place of t-butyl alcohol in the process of this Example, such as cyclohexyl alcohol, isopropyl alcohol, benzyl alcohol, n-pentanol, n-hexanol, or n-propanol, the respective esters are prepared, i.e., cyclohexyl 3,7,11-trimethyldodeca-2,4,10-trienoate
isopropyl 3,7,11-trimethyldodeca-2,4,10-trienoate
benzyl 3,7,11-trimethyldodeca-2,4,10-trienoate
n-pentyl 3,7,11-trimethyldodeca-2,4,10-trienoate
n-hexyl 3,7,11-trimethyldodeca-2,4,10-trienoate
n-propyl 3,7,11-trimethyldodeca-2,4,10-trienoate

EXAMPLE 5

To a solution of 0.5 g. of trans/cis 3,7,11-trimethyldodeca-2,4,10-trienoic acid in 15 ml. of benzene is added with stirring an equivalent amount of potassium bicarbonate. The mixture is stirred until the evolution of carbon dioxide ceases and then evaporated to yield potassium 3,7,11-trimethyldodeca-2,4,10-trienoate.

Alternatively, acid salts can be prepared by titrating the acid with an organic solution or aqueous organic solution of the desired metal.

EXAMPLE 6

One gram of 3,7,11-trimethyltrideca-2,4,10-trienoic acid in 30 ml. of benzene and one mol of sodium hydride is stirred about two hours and then a slight excess of oxalyl chloride is added at about 0° and stirred for one hour. The product is worked up by removal of solvent in vacuo and extraction with pentane to yield 3,7,11-trimethyltrideca-2,4,10-trienoyl chloride.

EXAMPLE 7

A. To magnesium propynylide (15 g.) in 150 ml. of ether is slowly added 0.3 moles of 3,7-dimethyloct-6-en-1-al and the mixture then stirred overnight. Saturated aqueous ammonium chloride is added and the layers separated. The organic phase, combined with ether backwashings of aqueous phase, is washed with water, dried and solvent evaporated to yield 6,10-dimethyl-9-undecen-2-yn-4-ol which can be purified by chromatography.

B. A mixture of 18.5 g. of the alkynyl alcohol of part A, 80 g. of triethylorthoacetate and 0.7 g. of propionic acid is refluxed under a spinning band column to remove ethanol as it is formed. After the elimination of ethanol is about complete, the crude reaction product is distilled under vacuum to yield ethyl 3,7,11-trimethyldodeca-3,4,10-trienoate. Alternatively, the crude reaction product is purified by chromotography on silica.

C. A solution of 1.0 g. of the allenic ester of part B in 20 ml. of ethanol is treated with 4 ml. of aqueous 2N sodium hydroxide and left at room temperature for several minutes. The mixture is then poured into pentane and washed with saturated brine and separated.

Evaporation of the organic phase yields ethyl 3,7,11-trimethyldodeca-2,4,10-trienoate.

EXAMPLE 8

The process of Example 7, part A, is repeated using each of the aldehydes under column I as the starting material to yield the respective alkynyl alcohol under column IV, each of which is reacted with triethylorthoacetate using the process of Example 7, part B, to prepare the respective allenic ester under column V.

IV 6,10-dimethyl-9-dodecen-2-yn-4-ol
6-methyl-10-ethyl-9-dodecen-2-yn-4-ol
6,10-diethyl-9-dodecen-2-yn-4-ol
7,11-dimethyl-10-dodecen-2-yn-4-ol
6,9-dimethyl-8-decen-2-yn-4-ol
6,9-dimethyl-8-undecen-2-yn-4-ol
5,9-dimethyl-8-decen-2-yn-4-ol

V ethyl 3,7,11-trimethyltrideca-3,4,10-trienoate
ethyl 3,11-dimethyl-7-ethyltrideca-3,4,10-trienoate
ethyl 3-methyl-7,11-diethyltrideca-3,4,10-trienoate
ethyl 3,8,12-trimethyltrideca-3,4,11-trienoate
ethyl 3,7,10-trimethylundeca-3,4,9-trienoate
ethyl 3,7,10-trimethyldodeca-3,4,9-trienoate
ethyl 3,6,10-trimethylundeca-3,4,9-trienoate Using the process of Example 7, part C, each of the allenic esters under column V is rearranged by treatment with aqueous sodium hydroxide to produce the respective α,β-unsaturated ester.

EXAMPLE 9

To 126 mg. of a 57% dispersion of sodium hydride in oil is added pentane. The pentane is removed and the sodium hydride washed several times with pentane. To the washed sodium hydride is added 582 mg. of diethyl acetyl-methylphosphonate (IIA; R' is ethyl, $R^1$ is methyl, $R^{12}$ is hydrogen) in 5 ml. of tetrahydrofuran at −10° under argon. After several minutes, the solution is transferred to a solution of 425 mg. of 3,7-dimethyloct-6-en-1-al in about 4 ml. of dry tetrahydrofuran under argon over a period of about 20 minutes at room temperature. After about 2 hours, water is added followed by addition of ether and the layers separated. The organic layer is washed with saturated sodium chloride, dried over sodium sulfate and evaporated under reduced pressure to yield 6,10-dimethylundeca-3,9-dien-2-one.

EXAMPLE 10

One gram of triphenylphosphineacetylmethylene and 425 mg. of 3,7-dimethylnon-6-en-1-al are dissolved in 10 ml. toluene and refluxed under nitrogen overnight. The toluene is distilled off and the formed triphenylphosphine oxide crystallized by addition of pentane. Filtration and evaporation of the pentane gives a residue, which is further purified by preparative thin layer chromatography to yield 6,10-dimethyldodeca-3,9-dien-2-one.

EXAMPLE 11

41 grams of 3,7-dimethyloct-6-en-1-al and 80 g. of recrystallized (ethyl acetate) triphenylphosphineacetyl-methylene [Ramirez et al., *J. Org. Chem.* 22, 41 (1957)] are refluxed in one liter of dry toluene for 18 hours, under nitrogen. Most of the solvent is removed in vacuo, 500 ml. pentane is added and the mixture filtered. The flask and the triphenylphosphine oxide filter cake are washed several times with pentane. The filtrate is concentrated under vacuum to yield 6,10-dimethylundeca-3,9-dien-2-one.

EXAMPLE 12

Using the process of either of Example 9, 10 or 11, each of the aldehydes under column I is converted into the respective di-unsaturated ketone under column VI.

VI 6,10-dimethyldodeca-3,9-dien-2-one
6-methyl-10-ethyldodeca-3,9-dien-2-one
6,10-diethyldodeca-3,9-dien-2-one
7,11-dimethyldodeca-3,10-dien-2-one
6,9-dimethyldeca-3,8-dien-2-one
6,9-dimethylundeca-3,8-dien-2-one
5,9-dimethyldeca-3,8-dien-2-one

EXAMPLE 13

The carbanion of diethyl carbomethoxymethyl phosphonate is reacted with 6,10-dimethylundeca-3,9-dien-2-one and each of the ketones under column VI using the procedure of either Example 1 or 9 to prepare the respective methyl esters under column VII.

VII methyl 3,7,11-trimethyldodeca-2,4,10-trienoate
methyl 3,7,11-trimethyltrideca-2,4,10-trienoate
methyl 3,11-dimethyl-7-ethyltrideca-2,4,10-trienoate
methyl 3-methyl-7,11-diethyltrideca-2,4,10-trienoate
methyl 3,8,12-trimethyltrideca-2,4,11-trienoate
methyl 3,7,10-trimethylundeca-2,4,9-trienoate
methyl 3,7,10-trimethyldodeca-2,4,9-trienoate
methyl 3,6,10-trimethylundeca-2,4,9-trienoate

EXAMPLE 14

Anhydrous hydrogen chloride is bubbled into 100 ml. of dry carbon tetrachloride at 0° until six equivalent is taken up. Five grams of trans ethyl 3,7,11-trimethyldodeca-2,4,10-trienoate is added and the resulting mixture allowed to stand for about 48 hours at 0°. The mixture is evaporated under reduced pressure to yield trans ethyl 11-chloro-3,7,11-trimethyldodeca-2,4-dienoate which is purified by chromatography.

The above process is repeated using each of the unsaturated esters under Column II to prepare the respective compound under Column VIII.

VIII ethyl 11-chloro-3,7,11-trimethyltrideca-2,4-dienoate,
ethyl 11-chloro-3,11-dimethyl-7-ethyltrideca-2,4-dienoate,
ethyl 11-chloro-7,11-diethyl-3-methyltrideca-2,4-dienoate,
ethyl 12-chloro-3,8,12-trimethyltrideca-2,4-dienoate,
ethyl 10-chloro-3,7,10-trimethylundeca-2,4-dienoate,
ethyl 10-chloro-3,7,10-trimethyldodeca-2,4-dienoate, and
ethyl 10-chloro-3,6,10-trimethylundeca-2,4-dienoate.

Each of the esters under col. VII is used as the starting material in the process of this example to prepare the hydrochlorides under col. IX.

IX methyl 11-chloro-3,7,11-trimethyldodeca-2,4-dienoate,
methyl 11-chloro-3,7,11-trimethyltrideca-2,4-dienoate,
methyl 11-chloro-3,11-dimethyl-7-ethyltridec-2,4-dienoate,
methyl 11-chloro-3-methyl-7,11-diethyltrideca-2,4-dienoate,
methyl 12-chloro-3,8,12-trimethyltrideca-2,4-dienoate,
methyl 10-chloro-3,7,10-trimethylundeca-2,4-dienoate,
methyl 10-chloro-3,7,10-trimethyldodeca-2,4-dienoate, and
methyl 10-chloro-3,6,10-trimethylundeca-2,4-dienoate.

EXAMPLE 15

Each of benzyl 3,7,11-trimethyltrideca-2,4,10-trienoate, isopropyl 3,7,11-trimethyldodeca-2,4,10-trienoate, cyclohexyl 3,7,11-trimethyldodeca-2,4,10-trienoate and n-hexyl 3,7,10-trimethylundeca-2,4,9-trienoate is used as the starting material in the procedure of Example 14 to prepare the respective compound, that is —
benzyl 11-chloro-3,7,11-trimethyltrideca-2,4-dienoate,
isopropyl 11-chloro-3,7,11-trimethyldodeca-2,4-dienoate,
cyclohexyl 11-chloro-3,7,11-trimethyldodeca-2,4-dienoate, and
n-hexyl 10-chloro-3,7,10-trimethylundeca-2,4-dienoate.

EXAMPLE 16

One gram of trans ethyl 3,7,11-trimethyldodeca-2,4,10-trienoate is added to a solution of 1 equiv. of dry hydrogenfluoride in dry tetrahydrofuran. The mixture is allowed to stand at 0° for 15 hours and is then washed with water, dried and evaporated under reduced pressure to yield trans ethyl 11-fluoro-3,7,11-trimethyldodeca-2,4-dienoate which can be purified by chromatography.

EXAMPLE 17

The process of Example 14 is repeated with the exception of using dry hydrogen bromide in place of hydrogen chloride to yield trans ethyl 11-bromo-3,7,11-trimethyldodeca-2,4-dienoate.
By treating the 11-bromide with anhydrous silver fluoride in acetonitrile under reflux conditions for about 6 hours, there is prepared trans ethyl 11-fluoro-3,7,11-trimethyldodeca-2,4-dienoate.

EXAMPLE 18

Chlorine gas is bubbled into 200 ml. of carbon tetrachloride at 0° until one equivalent is taken up. Twenty-five grams of trans ethyl 3,7,11-trimethyldodeca-2,4,10-trienoate is added and the mixture is then stirred and then allowed to stand at about 0° for 24 hours. The mixture is then evaporated to yield trans ethyl 10,11-dichloro-3,7,11-trimethyldodeca-2,4-dienoate which can be purified by chromatography.

EXAMPLE 19

To a mixture of 5 g. of trans ethyl 3,7,11-trimethyldodeca-2,4,10-trienoate in 100 ml. of fluorotrichloromethane is slowly added 1 equiv. of dry fluorine in about one hour at about −78°. After stirring the mixture at this temperature for about 16 hours, the resultant mixture is evaporated and chromatographed on silica to yield trans ethyl 10,11-difluoro-3,7,11-trimethyldodeca-2,4-dienoate.

By using bromine in the process of Example 18 there is prepared trans ethyl 10,11-dibromo-3,7,11-trimethyldodeca-2,4-dienoate.

EXAMPLE 20

To a mixture of 1.9 g. of mercuric acetate, 6 ml. of water and 20 ml. of tetrahydrofuran is added 1.49 g. of trans ethyl 3,7,11-trimethyldodeca-2,4,10-trienoate slowly. After addition is complete, the reaction mixture is stirred for about 20 minutes. The mixture is cooled to about 0° and 6 ml. of aqueous sodium hydroxide (3 molar) is added followed by 0.49 g. of sodium borohydride in aqueous sodium hydroxide (about 3 molar). The mixture is stirred for about 30 minutes. The mixture is then decanted, concentrated, diluted with water and then extracted with ether. The ethereal extract is washed with water, dried over magnesium sulfate and the product chromatographed on silica gives ethyl 11-hydroxy-3,7,11-trimethyldodeca-2,4-dienoate (trans).

The above process is repeated using each of the unsaturated esters under Column II to prepare the respective compound under Column X.

X ethyl 11-hydroxy-3,7,11-trimethyltrideca-2,4-dienoate,
ethyl 11-hydroxy-3,11-dimethyl-7-ethyltrideca-2,4-dienoate,
ethyl 11-hydroxy-7,11-diethyl-3-methyltrideca-2,4-dienoate,
ethyl 12-hydroxy-3,8,12-trimethyltrideca-2,4-dienoate,
ethyl 10-hydroxy-3,7,10-trimethylundeca-2,4-dienoate,
ethyl 10-hydroxy-3,7,10-trimethyldodeca-2,4-dienoate, and
ethyl 10-hydroxy-3,6,10-trimethylundeca-2,4-dienoate.

EXAMPLE 21

Each of the esters under Column VII is used as the starting material in the process of Example 20 to prepare the respective hydroxyl under Column XI.

XI methyl 11-hydroxy-3,7,11-trimethyldodeca-2,4-dienoate,
methyl 11-hydroxy-3,7,11-trimethyltrideca-2,4-dienoate,
methyl 11-hydroxy-3,11-dimethyl-7-ethyltrideca-2,4-dienoate,
methyl 11-hydroxy-3-methyl-7,11-diethyltrideca-2,4-dienoate,
methyl 12-hydroxy-3,8,12-trimethyltrideca-2,4-dienoate,
methyl 10-hydroxy-3,7,10-trimethylundeca-2,4-dienoate,
methyl 10-hydroxy-3,7,10-trimethyldodeca-2,4-dienoate, and
methyl 10-hydroxy-3,6,10-trimethylundeca-2,4-dienoate.

EXAMPLE 22

Each of benzyl 3,7,11-trimethyltrideca-2,4,10-trienoate, isopropyl 3,7,11-trimethyldodeca-2,4,10-trienoate, cyclohexyl 3,7,11-trimethyldodeca-2,4,10-trienoate and n-hexyl 3,7,10-trimethylundeca-2,4,9-trienoate is used as the starting material in the process of Example 20 to prepare the respective hydroxy, that is — benzyl 11-hydroxy-3,7,11-trimethyltrideca-2,4-dienoate,
isopropyl 11-hydroxy-3,7,11-trimethyldodeca-2,4-dienoate,
cyclohexyl 11-hydroxy-3,7,11-trimethyldodeca-2,4-dienoate, and
n-hexyl 10-hydroxy-3,7,10-trimethylundeca-2,4-dienoate.

EXAMPLE 23

To a solution of 2 g. of trans ethyl 3,7,11-trimethyldodeca-2,4,10-trienoate in 20 ml. of ethanol, cooled to 0° in an ice bath, is added a suspension of 2.32 g. of mercuric acetate in 50 ml. of ethanol over 15 minutes. The reaction mixture is stirred for two hours and then, with cooling, 1.22 g. of potassium hydroxide in 20 ml. of ethanol is added. Then 0.139 g. of sodium borohydride is added in small portions and stirring continued for 30 minutes. The solution is decanted, then concentrated to half volume, diluted with 100 ml. of water and extracted with ether (3 × 50). The ethereal phase is washed with water, dried over magnesium sulfate and the crude product chromatographed on silica using hexane:ether to yield trans ethyl 11-ethoxy-3,7,11-trimethyldodeca-2,4-dienoate.

EXAMPLE 24

A mixture of 1 g. of trans ethyl 11-hydroxy-3,7,11-trimethyldodeca-2,4-dienoate, 10 ml. of acetic anhydride and 0.5 g. of dry sodium acetate is refluxed for about 5 hours. After cooling, excess anhydride is removed by vacuum and the residue extracted with ether. The ethereal extract is washed, dried over magnesium sulfate and evaporated to yield the corresponding acetate, trans ethyl 11-acetoxy-3,7,11-trimethyldodeca-2,4-dienoate.

EXAMPLE 25

A mixture of 2 g. of dry trans ethyl 11-hydroxy-3,7,11-trimethyldodeca-2,4-dienoate, 15 ml. of acetyl chloride and 20 ml. of dry pyridine under nitrogen is heated on a steam bath for about 6 hours. After cooling, the mixture is concentrated under vacuum and the residue taken up in ether. The ethereal extract is washed, dried over magnesium sulfate and evaporated to yield the corresponding acetate, trans ethyl 11-acetoxy-3,7,11-trimethyldodeca-2,4-dienoate.

The process of this example is repeated with the exception of using triethylamine in place of pyridine to yield the 11-acetate.

EXAMPLE 26

One gram of trans ethyl 11-hydroxy-3,7,11-trimethyldodeca-2,4-dienoate in 10 ml. of diglyme is added dropwise to a slurry of 1 g. of sodium hydride in 10 ml. of diglyme under nitrogen. To this mixture is added 0.9 g. of cyclohexylchloride. The reaction mixture is stirred at about 25° for 30 minutes and then quenched in ice water. The organic phase is separated and aqueous phase re-extracted with ether. The organic materials are washed with water, dried over sodium sulfate and evaporated to yield the cyclohexyl ether of trans ethyl 11-hydroxy-3,7,11-trimethyldodeca 2,4-dienoate.

By using each of benzyl chloride and cyclopentyl chloride in the foregoing procedure, the corresponding benzyl ether and cyclopentyl ether is prepared.

EXAMPLE 27

By use of the procedure of Example 25, ethyl 11-hydroxy-3,7,11-trimethyldodeca-2,4-dienoate is converted into the corresponding 11-chloroacetate, 11-dichloroacetate and 11-trichloroacetate using chloroacetyl chloride, -dichloroacetyl chloride and trichloroacetyl chloride, respectively.

The respective 11-trifluoroacetate, propionate, n-butanoate, n-pentanoate and n-hexanoate esters of ethyl 11-hydroxy-3,7,11-trimethyldodeca-2,4-dienoate are prepared according to the process of Example 24 using trifluoroacetic anhydride, propionic anhydride, n-butyric anhydride, n-pentanioc anhydride and n-hexanoic anhydride or according to the process of Example 25 using the corresponding acid chloride.

EXAMPLE 28

A mixture of 20 ml. of dry formic acid and 2 g. of trans ethyl 3,7,11-trimethyldodeca-2,4,10-trienoate is heated at 50° for 2 hours and then poured onto ice cold potassium bicarbonate solution. The reaction is worked up by extraction with ether, washing the ethereal extract, drying over magnesium sulfate and evaporation to yield the formate of trans ethyl 11-hydroxy-3,7,11-trimethyldodeca-2,4-dienoate.

Using the above process, the formates of formula A are prepared from the corresponding precursor of formula B having a terminal olefinic bond.

EXAMPLE 29

Fifteen grams of mercuric acetate in 50 ml. of dry ethanol is added to 12 g. of trans ethyl 3,7,11-trimethyldodeca-2,4,10-trienoate in 30 ml. of dry ethanol cooled in an ice bath. The temperature is allowed to come to room temperature by standing overnight. Then the mixture is cooled to 0°, 10 g. of potassium hydroxide in 150 ml. of ethanol is added followed by addition of 1.0 g. of sodium borohydride in small portions. After about 30 minutes at 0°, water is added and mixture left at room temperature for 2 hours. The mixture is filtered, filtrate concentrated and extracted with ether. The ethereal extract is washed, dried, and evaporated to yield trans ethyl 11-ethoxy-3,7,11-trimethyldodeca-2,4-dienoate which is purified by distillation or chromatography.

By using methanol in the foregoing process in place of ethanol, there is prepared the respective 11-methyl ether. In the same way, each of isopropanol, t-butanol, and n-propanol is added to the terminal double bond to prepare:

ethyl 11-isopropoxy-3,7,11-trimethyldodeca-2,4-dienoate,
ethyl 11-t-butoxy-3,7,11-trimethyldodeca-2,4-dienoate, and
ethyl 11-n-propoxy-3,7,11-trimethyldodeca-2,4-dienoate

EXAMPLE 30

Each of the tri-unsaturated esters under col. VII is used as the starting material in the process of Example 21 or 29 to yield the respective ethoxy substituted compound under col. XII.

XII methyl 11-ethoxy-3,7,11-trimethyldodeca-2,4-dienoate,
methyl 11-ethoxy-3,7,11-trimethyltrideca-2,4-dienoate,
methyl 11-ethoxy-3,11-dimethyl-7-ethyltrideca-2,4-dienoate,
methyl 11-ethoxy-3-methyl-7,11-diethyltrideca-2,4-dienoate,
methyl 12-ethoxy-3,8,12-trimethyltrideca-2,4-dienoate,
methyl 10-ethoxy-3,7,10-trimethylundeca-2,4-dienoate,
methyl 10-ethoxy-3,7,10-trimethyldodeca-2,4-dienoate, and
methyl 10-ethoxy-3,6,10-trimethylundeca-2,4-dienoate.

EXAMPLE 31

A mixture of 1 g. of trans methyl 11-ethoxy-3,7,11-trimethyldodeca-2,4-dienoate, 60 ml. of methanol, 0.5 g. of potassium hydroxide and 6 ml. of water is heated at reflux for about 8 hours. The mixture is then diluted with water, neutralized and extracted with ether. The organic phase is washed with water, dried over sodium sulfate and evaporated to yield trans 11-ethoxy-3,7,11-trimethyldodeca-2,4-dienoic acid.

EXAMPLE 32

Using each of the esters under Column II as the starting material in the process of either Example 22 or 29, there is prepared the respective substituted ester under Column XIII.

XIII ethyl 11-ethoxy-3,7,11-trimethyldodeca-2,4-dienoate;
ethyl 11-ethoxy-3,7,11-trimethyltrideca-2,4-dienoate,
ethyl 11-ethoxy-3,11-dimethyl-7-ethyl trideca-2,4-dienoate,
ethyl 11-ethoxy-7,11-diethyl-3-methyltrideca-2,4-dienoate,
ethyl 12-ethoxy-3,8,12-trimethyltrideca-2,4-dienoate,
ethyl 10-ethoxy-3,7,10-trimethylundeca-2,4-dienoate,
ethyl 10-ethoxy-3,7,10-trimethyldodeca-2,4-dienoate, and
ethyl 10-ethoxy-3,6,10-trimethylundeca-2,4-dienoate.

EXAMPLE 33

A. To a mixture of 50 g. of 7-methoxy-3,7-dimethyloctan-1-al, 75 g. of diethyl 3-ethoxycarbonyl-2-methylprop-2-enyl phosphonate (49% trans), and 500 ml. of dimethylformamide, under nitrogen, at 0°, and with stirring, is slowly added 9 g. of sodium in 250 ml. of ethanol. After addition is complete, the reaction is allowed to continue one hour at room temperature. The reaction is worked up with hexane, filtered through Florisil and filtrate evaporated to yield trans(2), trans(4) and cis(2), trans(4) ethyl 11-methoxy-3,7,11-trimethyldodeca-2,4-dienoate (about 60% trans, trans).

B. A mixture of 45 g. of the ethyl ester of part A, 350 ml. of ethanol, 100 ml. of water and 70 ml. of 50% aqueous NaOH is refluxed for 22 hours. Ethanol is then removed under reduced pressure, water added followed by extraction with ether. The aqueous phase is adjusted to about pH 8 using aqueous HCl and 31 g. of S-benzyl-isothiouronium hydrochloride in water is added. The thus-formed salt is filtered, washed with water, recrystallized from aqueous methanol (twice) and then treated with aqueous HCl/ether and worked up to yield 11-methoxy-3,7,11-trimethyldodeca-2,4-dienoic acid which crystallizes on cooling.

C. The acid (0.5 g.) of part B is methylated using diazomethane in ether, followed by chromatography on prep. TLC and distillation (short path) to prepare methyl 11-methoxy-3,7,11-trimethyldodeca-2,4-dienoate [95.2% trans(2), trans(4)]. In the same way, using diazoethane is prepared ethyl 11-methoxy-3,7,11-trimethyldodeca-2,4-dienoate [95.2% trans(2), trans(4)].

EXAMPLE 34

To 0.5 g. of the acid of Example 33 in 10 ml. of benzene, under nitrogen, is added 0.055 g. of sodium hydride. After stirring at room temperature for 15 minutes, 0.17 ml. of oxalyl chloride is added followed by stirring for 2.5 hours. Then 2 ml. of isopropanol is added. After about 3 hours, the reaction is worked up by extraction with ether, washing with sodium bicarbonate and brine, drying over calcium sulfate and isolation to yield isopropyl 11-methoxy-3,7,11-trimethyldodeca-2,4-dienoate (about 91% trans, trans).

EXAMPLE 35

To 0.5 g. of the acid of Example 33 in 10 ml. of benzene, under nitrogen is added 0.17 ml. of oxalyl chloride which is stirred for about 45 minutes and then allowed to stand 2 hours. Two ml. of isopropanol is added. After 3 hours, ether is added and organic layer separated. The organic layer is washed with aqueous sodium bicarbonate and brine, dried over calcium sulfate and concentrated under reduced pressure to yield isopropyl 11-methoxy-3,7,11-trimethyldodeca-2,4-dienoate (about 91% trans, trans) which can be purified by chromatography and distillation.

Using the foregoing precedure, each of 3-thiacyclohexanol, 2,2,2-trifluoroethanol, t-butanol, 2-methoxyethanol, 2-methylthioethanol and s-butanol provides 3'-thiacyclohexyl 11-methoxy-3,7,11-trimethyldodeca-2,4-dienoate, 2',2',2'-trifluoroethyl 11-methoxy-3,7,11-trimethyldodeca-2,4-dienoate, t-butyl 11-methoxy-3,7,11-trimethyldodeca-2,4-dienoate, 2'-methoxyethyl 11-methoxy-3,7,11-trimethyldodeca-2,4-dienoate, 2'-methylthioethyl 11-methoxy 3,7,11-trimethyldodeca-2,4-dienoate, and s-butyl 11-methoxy-3,7,11-trimethyldodeca-2,4-dienoate. Each of the esters is primarily the trans(2), trans(4) isomer.

EXAMPLE 36

Sodium ethoxide (prepared from 0.2 g. of sodium and 12 ml. of ethanol) is slowly added to a mixture of 1.1 g. of 7-ethoxy-3,7-dimethyloctan-1-al, diethyl 3-ethoxycarbonyl-2-methylprop-2-enyl phosphonate and 50 ml. of dimethylformamide, with stirring, under nitrogen, at 0°. The reaction is stirred for 1.5 hours after addition is complete and then worked up by extraction with ether to yield ethyl 11-ethoxy-3,7,11-trimethyldodeca-2,4-dienoate, mostly trans(2), trans(4), which can be further purified by chromatography and distillation.

EXAMPLE 37

To a mixture of 10 g. of 7-methoxy-3,7-dimethyloctan-1-al, 17 g. of diethyl 3-ethoxycarbonyl-2-methylprop-2-enyl phosphonate (77% trans), and 150 ml. of dimethylformamide, under nitrogen, 0°, with stirring, is added sodium isopropanolate (prepared from 1.5 g. of sodium in 150 ml. of isopropanol). After addition is complete, the reaction is stirred for 18 hours at room temperature and then worked up by extraction with hexane to yield isopropyl 11-methoxy-3,7,11-trimethyldodeca-2,4-dienoate (mostly trans-2,trans-4), which can be chromatographed and distilled for further purification.

EXAMPLE 38

A mixture of 5 g. of hydroxycitronellal (7-hydroxy-3,7-dimethyloctan-1-al), 8.5 g. of di-isopropyl 3-ethoxycarbonyl-2-methylprop-2-enyl phosphonate, and 40 ml. of dimethylformamide, under nitrogen and cooled in an ice-bath, is stirred for 0.5 hour and then ground NaOH (1.165 g.) is added. The reaction mixture is stirred at room temperature for three hours and then hexane/water (1/1) added. The organic layer is washed with water and brine, dried over calcium sulfate and concentrated. The concentrate is filtered through Florisil using hexane and hexane/ether. The filtrate is concentrated and then distilled to yield ethyl 11-hydroxy-3,7,11-trimethyldodeca-2,4-dienoate (about 85% trans-2, trans-4).

The process of this example is repeated with the exception of using di-isopropyl 3-isopropoxycarbonyl-2-methylprop-2-enyl phosphonate to prepare isopropyl 11-hydroxy-3,7,11-trimethyldodeca-2,4-dienoate, about 78% trans(2), trans(4) and 21% cis(2), trans(4).

EXAMPLE 39

To 40 ml. of ice cold isopropanol is added 2.49 g. of acetyl chloride. The resulting solution is stirred at 0° for 15 min. and 1.0 g. of trans isopropyl 3,7,11-trimethyldodeca 2,4,10-trienoate added. The solution is stirred for 1 hour at 0° and for 48 hours at 25°. Solvent is removed under reduced pressure and the concentrate taken up in hexane. The hexane solution is washed with water until the aqueous wash is neutral and then with brine. The solution is dried over calcium sulfate and solvent evaporated to yield trans isopropyl 11-chloro-3,7,11-trimethyldodeca-2,4-dienoate.

EXAMPLE 40

A. 100 grams of 3,7-dimethyloct-6-en-1-ol is dissolved in 150 ml. of pyridine and 100 ml. of acetate anhydride and left at room temperature for about 48 hours. Then the mixture is extracted with ether and the ethereal extracts washed with water, 10% aqueous HCl and brine to yield 1-acetoxy-3,7-dimethyloct-6-ene which is purified by distillation.

B. 150 grams of mercuric acetate in 400 ml. of dry ethanol is added to 100 g. of 1-acetoxy-3,7-dimethyloct-6-ene (citronellol acetate) in 200 ml. of dry ethanol cooled in an ice bath. The temperature is allowed to come to room temperature by standing overnight. Then the mixture is cooled to 0°, 100 g. of potassium hydroxide in 1.5 l. of ethanol is added followed by addition of 10 g. of sodium borohydride in small portions. After about 30 minutes at 0°, water (100 ml.) is added and mixture left at room temperature for two hours. The mixture is filtered, filtrate concentrated and extracted with ether. The ethereal extract is washed, dried and evaporated to yield 7-ethoxy-3,7-dimethyloctan-1-ol which is purified by distillation or chromatography.

By using methanol in the foregoing process in place of ethanol, there is obtained 7-methoxy-3,7-dimethyloctan-1-ol.

C. A mixture of 1.9 of 7-ethoxy-3,7-dimethyloctan-1-ol and 10 ml. of pyridine is added to a suspension of 8.0 g. of chromium trioxide in 100 ml. of pyridine with stirring under nitrogen. After about 4 hours at room temperature, the reaction is poured into saturated sodium bicarbonate and worked up with ether followed by washing with 2N NaOH, water, 10% HCl, water and brine and evaporated under reduced pressure to dryness and then filtered with hexane to yield 7-ethoxy-3,7-dimethyloctan-1-al.

D. A mixture of 9.0 g. of 7-ethoxy-3,7-dimethyloctan-1-al and 15 g. of triphenylphosphineacetylmethylene in 100 ml. of dry toluene, under nitrogen, is refluxed for 20 hours. Thereafter, the toluene is evaporated and pentane added to remove triphenylphosphine. After concentration, the product is distilled to yield 10-ethoxy-6,10dimethylundec-3-en-2-one. The thus-prepared ketone is reacted with the carbanion of diethyl carbethoxymethylphosphonate using the procedure of Example 1 or 9 to prepare ethyl-11-ethoxy-3,7,11-trimethyldodeca-2,4-dienoate.

EXAMPLE 41

Each of the aldehydes under col. XIV is reacted with the carbanion of di-isopropyl 3-isopropoxycarbonyl-2-methylprop-2-enyl phosphonate using the procedure of Example 38 to prepare the respective isopropyl ester under col. XV.

XIV 3,6,7-trimethyloct-6-en-1-al
3,6,7-trimethylnon-6-en-1-al
2,5-dimethylhex-4-en-1-al
2,4,5-trimethyl-4-en-1-al
3,5,6-trimethylhept-5-en-1-al
2,5,6-trimethylhept--methoxy--en--trimethyldeca-2,4-al
3,8-dimethylnon-7-en-1-al
3,9-dimethyldec-8-en-1-al

XV isopropyl 3,7,10,11-tetramethyldodeca-2,4,10-trienoate
isopropyl 3,7,10,11-tetramethyltrideca-2,4,10-trienoate
isopropyl 3,6,9-trimethyldeca-2,4,8-trienoate
3,6,8,9-tetramethyldeca-2,4,8-trienoate
isopropyl 3,7,9,10-tetramethylundeca-2,4,9-trienoate
isopropyl 3,6,9,10-tetramethylundeca-2,4,9-trienoate
isopropyl 3,7,12-trimethyltrideca-2,4,11-trienoate
isopropyl 3,7,13-trimethyltetradeca-2,4,12-trienoate The reaction of the aldehydes under col. XIV with the carbanion of diethyl 3-methoxycarbonyl-2-methylprop-2-enylphosphonate yields the respective methyl tri-unsaturated esters. In the same way the respective ethyl tri-unsaturated esters are prepared using diethyl 3-ethoxy-carbonyl-2-methylprop-2-enylphosphonate.

Hydrochlorinated derivatives of the above esters are prepared using the procedure of Example 14 or 39. For example, isopropyl 11-chloro-3,7,10,11-tetramethyldodeca-2,4-dienoate,
isopropyl 11-chloro-3,7,10,11-tetramethyltrideca-2,4-dienoate,
isopropyl 10-chloro-3,7,9,10-tetramethylundeca-2,4-dienoate, and
isopropyl 12-chloro-3,7,12-trimethyltrideca-2,4-dienoate.

Following the procedure of Example 23 or 29, methanol is added to the terminal double bond of each of the esters under col. XV to prepare:

isopropyl 11-methoxy-3,7,10,11-tetramethyldodeca-2,4-dienoate,
isopropyl 11-methoxy-3,7,10,11-tetramethyltrideca-2,4-dienoate,
isopropyl 9-mechoxy-3,6,9-trimethyldeca-,2,4-dienoate,
isopropyl 9-methoxy-3,6,8,9-tetramethyldecan-2,4-dienoate,
isopropyl 10-methoxy-3,7,9,10-tetramethylundeca-2,4-dienoate,
isopropyl 10-methoxy-3,6,9,10-tetramethylundeca-2,4-dienoate,
isopropyl 12-methoxy-3,7,12-trimethyltrideca-2,4-dienoate, and
isopropyl 13-methoxy-3,7,13-trimethyltetradeca-2,4-dienoate.

In the same way, ethanol is added to the terminal double bond to prepare the respective ethoxy substituted 2,4-dienoates. Using the procedure of Example 20, water is added to the terminal double bond to prepare the respective hydroxy-substituted 2,4-dienoate.

EXAMPLE 42

A. Eighty ml. of a 3M solution of methylmagnesium bromide in ether is added slowly to 31 g. of citronellal in 250 ml. of dry ether. The mixture is heated at reflux for about 1 hour, cooled to 0° and treated with saturated aqueous ammonium chloride until reaction subsides. The organic layer is separated and the aqueous layer extracted with ether. The organic layer and ether extracts are combined, washed with water and brine and dried over magnesium sulfate. Evaporation of the solvent gives 4,8-dimethylnon-7-en-2-ol.

B. A solution of 47 g. of 4,8-dimethylnon-7-en-2-ol in 250 ml. of methylene chloride is cooled to about 10° as a solution of 46.4 g. of sodium dichromate in 125 ml. of water is added. The mixture is at about 10° as a solution of 46.3 g. of sulfuric acid in 100 ml. of water is added over about 45 minutes. The mixture is allowed to attain room temperature and, after about 3 hours, the organic layer is separated and the aqueous layer is extracted with methylene chloride. The combined organic materials are washed with saturated potassium bicarbonate, water and saturated sodium chloride, dried over magnesium sulfate and evaporated to yield 4,8-dimethylnon-7-en-2-one.

The Grignard reaction of part A is repeated using each 3,7-dimethylnon-6-en-1-al, 3--methyl-7-ethylnon-6-en-1-al, 3,6,7-trimethyloct-6-en-1-al, 3,7,8-trimethylnon-7-en-1-al, 2,4,5-trimethylhex-4-en-1-al, 2,5-dimethylhex-4-en-1-al, 3,5,6-trimethylhept-5-en-1-al, 3,6-dimethylhept-5-en-1-al, 2,6-dimethylhept-5-en-1-al and 2,5,6-trimethylhept-5-en-1-al in place of citronellal to yield the respective secondary alcohol —

4,8-dimethyldec-7-en-2-ol
4-methyl-8-ethyldec-7-en-2-ol
4,7,8-trimethylnon-7-en-2-ol
4,8,9-trimethyldec-en-2-ol
3,5,6-trimethylhept-5-en-2-ol
3,6-dimethylhept-5-en-2-ol
4,6,7-trimethyloct-6-en-2-ol
4,7-dimethyloct-6-en-2-ol
3,7-dimethyloct-6-en-2-ol
3,6,7-trimethyloct-6-en-2-ol Each of the above alcohols is oxidized to prepare the respective ketone —

4,8-dimethyldec-7-en-2-one
4-methyl-8-ethyldec-7-en-2-one
4,7,8-trimethylnon-7-en-2-one
4,8,9-trimethyldec-8-en-2-one
3,5,6-trimethylhept-5-en-2-one
3,6-dimethylhept-5-en-2-one
4,6,7-trimethyloct-6-en-2-one
4,7-dimethyloct-6-en-2-one
3,7-dimethyloct-6-en-2-one
3,6,7-trimethyloct-6-en-2-one C. Each of the ketones of part B is reacted with the carbanion of diethyl 3-ethoxycarbonyl-2-methylprop-2-enyl phosphonate according to procedures above to prepare the respective tri-unsaturated ester i.e. — ethyl 3,5,7,11-tetramethyldodeca-2,4,10-trienoate
ethyl 3,5,7,11-tetramethyltrideca-2,4,10-trienoate
ethyl 3,5,7-trimethyl-11-ethyltrideca-2,4,10-trienoate
ethyl 3,5,7,10,11-pentamethyldodeca-2,4,10-trienoate
ethyl 3,5,7,11,12-pentamethyltrideca-2,4,11-trienoate
ethyl 3,5,6,8,9-pentamethyldeca-2,4,8-trienoate
ethyl 3,5,6,9-tetramethyldeca-2,4,8-trienoate
ethyl 3,5,7,9,10-pentamethylundeca-2,4,9-trienoate
ethyl 3,5,7,10-tetramethylundeca-2,4,9-trienoate
3,5,6,10-tetramethylundeca-2,4,9-trienoate
ethyl 3,5,6,9,10-pentamethylundeca-2,4,9-trienoate

EXAMPLE 43

A. Each of the ketones of part B of Example 42 is reacted with the carbanion of diethyl 3-ethoxycarbonyl-1,2-dimethylprop-2-enylphosphonate to prepare the respective trienoate — i.e.— ethyl 3,4,5,7,11-pentamethyldodeca-2,4,10-trienoate
ethyl 3,4,5,7,11-pentamethyltrideca-2,4,10-trienoate
ethyl 3,4,5,7-tetramethyl-11-ethyltrideca-2,4,10-trienoate
ethyl 3,4,5,7,10-11-hexamethyldodeca-2,4,10-trienoate
ethyl 3,4,5,7,11,12-hexamethyltrideca-2,4,11--trienoate
ethyl 3,4,5,6,8,9,]-hexamethyldeca-2,4,8-trienoate
ethyl 3,4,5,6,9-pentamethyldeca-2,4,8-trienoate
ethyl 3,4,5,7,9,10-hexamethylundeca-2,4,9-trienoate
ethyl 3,4,5,7,10-pentamethylundeca-2,4.9-trienoate
ethyl 3,4,5,6,10-pentamethylundeca-2,4,9-trienoate
ethyl 3,4,5,6,9,10-hexamethylundeca-2,4,9-trienoate B. Each of the aldehydes under col. I is reacted with the carbanion of diethyl 3-ethoxycarbonyl-1,2-dimethylprop-2-enyl phosphonate to prepare the respective trienoate, i.e. — ethyl 3,4,7,11-tetramethyltrideca-2,4,10-trienoate
ethyl 3,4,11-trimethyl-7-ethyltrideca-2,4,10-trienoate
ethyl 3,4-dimethyl-7,11-diethyltrideca-2,4,10-trienoate
ethyl 3,4,8,12-tetramethyltrideca-2,4,11-trienoate
ethyl 3,4,7,10-tetramethylundeca-2,4,9-trienoate
ethyl 3,4,7,10-tetramethyldodeca-2,4,9-trienoate
ethyl 3,4,6,10-tetramethylundeca-2,4,9-trienote By use of the procedure of part B of this example, other aldehydes of formula I ($R^{13}$ is hydrogen are converted into the respective ester of formula B' wherein $R^{13}$ is hydrogen and $R^{12}$ is methyl or other lower alkyl. Similarly following the procedure of part A of this example, other ketones of formula I ($R^{13}$ is lower alkyl) are converted into esters of formula B' wherein each of $R^{12}$ and $R^{13}$ is lower alkyl. Using the process of part C of Example 42 other esters of the present invention of formula B' wherein $R^{12}$ is hydrogen and $R^{13}$ is methyl or other lower alkyl can be prepared using a ketone of formula I ($R^{13}$ is lower alkyl) as the precursor.

C. Each of the esters of this example and Example 42 can be hydrolyzed to the free acid according to the procedure of Example 3 or 33. The acid or acid chloride can be reacted with an alcohol such as isopropanol, t-butanol, benzyl alcohol, and the like to prepare the other esters of the present invention.

EXAMPLE 44

Following the process of Example 35, 11-methoxy-3,7,11-trimethyldodeca-2,4-dienoic acid is esterified using each of cyclohexanol, n-propanol, i-butanol, benzyl alcohol, phenol n-hexanol, 3,3-dimethylpentan-1-ol, 2-methylpentan-1-ol, hexan-2-ol, 3-methylpentan-1-ol, p-ethylphenol, β-phenylethanol, 2-fluoroethano, 2,2-dichloroethanol, 2-chloropropan-1-ol, 2,2,2-trichloroethanl and p-methylthiophenol to prepare the respective ester.

cyclohexyl 11-methoxy-3,7,11-trimethyldodeca-2,4-dienoate
n-propyl 11-methoxy-3,7,11trimethyldodeca-2,4-dienoate
i-butyl 11-methoxy-3,7,11-trimethyldodeca-2,4-dienoate
benzyl 11-methoxy-3,7,11-trimethyldodeca-2,4-dienoate
phenyl 11-methoxy-3,7,11-trimethyldodeca-2,4-dienoate
n-hexyl 11-methoxy-3,7,11-trimethyldodeca-2,4-dienoate
3',3'-dimethylpentyl 11-methoxy-3,7,11-trimethyldodeca-2,4-dienoate
2'-methylpentyl 11-methoxy-3,7,11-trimethyldodeca-2,4-dienoate
hexan-2'-yl 11-methoxy-3,7,11-trimethyldodeca-2,4-dienoate
3'-methylpentyl 11-methoxy-3,7,11-trimethyldodeca-2,4-dienoate
p-ethylphenyl 11-methoxy-3,7,11-trimethyldodeca-2,4-dienoate
β-phenylethyl 11-methoxy-3,7,11-trimethyldodeca-2,4-dienoate
2'-fluoroethyl 11-methoxy-3,7,11-trimethyldodeca-2,4-dienoate
2',2'-dichloroethyl 11-methoxy-3,7,11-trimethyldodeca-2,4-dienoate
2'-chloropropyl 11-methoxy-3,7,11-trimethyldodeca-2,4-dienoate
2',2',2'-trichloroethyl 11-methoxy-3,7,11-trimethyldodeca-2,4-dienoate
p-methylthiophenyl 11-methoxy-3,7,11-trimethyldodeca-2,4-dienoate

EXAMPLE 45

To a solution of 0.5 g. of trans, trans 11-methoxy-3,7,11-trimethyldodeca-2,4-dienoic acid in 15 ml. of benzene is added, with stirring, an equivalent amount of potassium hydride. The mixture is stirred at room temperature for about 2 hours and then evaporated to give potassium 11-methoxy-3,7,11-trimethyldodeca-2,4-dienoate.

In place of KH, there can be used KOH, NaOH, and the like to form the corresponding salt.

EXAMPLE 46

Methanol is added to the terminal bond of ethyl 3,4,7,11-tetramethyldodeca-2,4,10-trienoate using the process of Example 23 or 29 to give ethyl 11-methoxy-3,4,7,11-tetramethyldodeca-2,4-dienoate. In the same manner, water is added to give ethyl 11-hydroxy-3,4,7,11-tetramethyldodeca-2,4-dienoate. Similarly, there is prepared ethyl 11-methoxy-3,5,7,11-tetramethyldodeca-2,4-dienoate and ethyl 11-hydroxy-3,5,7,11-tetramethyldodeca-2,4-dienoate from ethyl 3,5,7,11-tetramethyldodeca-2,4,10-trienoate. The hydrochloride, ethyl 11-chloro-3,4,7,11-tetramethyldodeca-2,4-dienoate and ethyl 11-chloro-3,5,7,11-tetramethyldodeca-2,4-dienoate are prepared from the trienoate using the process of Example 39.

EXAMPLE 47

To a solution of 1.8 g. of 6,10-dimethylundeca-3,9-dien-2-one in 20 ml. of ethanol, cooled to 0° by an ice bath is added a suspension of 2.32 g. of mercuric acetate in 50 ml. of ethanol over 15 minutes. The reaction mixture is stirred for 2 hours and then, with cooling, to −20°, 1.22 g. of potassium hydroxide in 20 ml. of ethanol is added. Then 0.139 g. of sodium borohydride is added in small portions and stirring continued for 30 minutes at −20°. The solution is decanted, then concentrated to half volume, diluted with 100 ml. of water and extracted with ether (3 × 50). The ethereal phase is washed with water, dried over magnesium sulfate and the crude product chromatographed on silica to yield 10-ethoxy-6,10-dimethylundec-3-en-2-one.

The process of this example is repeated using each of the compounds under column VI as the starting material to prepare the respective ethoxy substituted compound under column XVI.

XVI 10-ethoxy-6,10-dimethyldodec-3-en-2-one
10-ethoxy-6-methyl-10-ethyldodec-3-en-2-one
10-ethoxy-6,10-diethyldodec-3-en-2-l -one
11-ethoxy-7,11-dimethyldodec-3-en-2-one
9-ethoxy-6,9-dimethyldec-3-en-2-l -one
9-ethoxy-6,9-dimethylundec-3-en-2-one
9-ethoxy-5,9-dimethyldec-3-en-2-one Following the process of Example 13, 10-ethoxy-6,10-dimethylundec-3-en-2-one is converted into methyl 11-ethoxy-3,7,11-trimethyldodeca-2,4-dienoate. Reaction of 10-ethoxy-6,10-dimethylundec-3-en-2-one with the carbanion of diethyl carboethoxymethylphosphonate yields ethyl 11-ethoxy-3,7,11-trimethyldodeca-2,4-dienoate.

By using other alcohols in the process of this example in lieu of ethanol, such as methanol, etc., the respective ethers are obtained, e.g., 10-methoxy-6,10-dimethylundec-3-en-2-one.

B. The process of part A is repeated using the starting material 3,7-dimethyloct-6-en-1-al and each of the aldehydes under column I or the acetal thereof to prepare the respective compounds under column XVII.

XVII 7-ethoxy-3,7-dimethyloctan-1-al
7-ethoxy-3,7-dimethylnonan-1-al
7-ethoxy-3-ethyl-7-methylnonan-1-al
7-ethoxy-3,7-diethylnonan-1-al
8-ethoxy-4,8-dimethylnonan-1-al
6-ethoxy-3,6-dimethylheptan-1-al
6-ethoxy-3,6-dimethyloctan-1-al
6-ethoxy-2,6-dimethylheptan-1-al Using 7-ethoxy-3,7-dimethyloctan-1-al as the starting material in the process of either Example 9, 10 or 11, there is prepared 10-ethoxy-6,10-dimethylundec-3-en-2-one.

EXAMPLE 49

To a solution of 2 g. of methyl 3,7,11-trimethyldodeca-2,4,10-trienoate and 20 ml. of dry ether, at −78°, is added slowly about 0.4 g. of lithium aluminum hydride in dry ether. The mixture is allowed to stand about 1 hour after addition is complete and then allowed to warm up to room temperature. Then 2.5 ml. of acetic acid is added. The mixture is then washed with ice water and the organic phase separated, which is dried over magnesium sulfate and evaporated to yield 3,7,11-trimethyldodeca-2,4,10-trien-1-ol.

By use of the process of this example, each of the esters under Column II or VII is reduced to prepare the respective allylic alcohol, i.e., 3,7,11-trimethyltrideca-2,4,10-trien-1-ol,
3,11-dimethyl-7-ethyltrideca-2,4,10-trien-1-ol,
7,11-diethyl-3-methyltrideca-2,4,10-trien-1-ol,
3,8,12-trimethyltrideca-2,4,11-trien-1-ol,
3,7,10-trimethylundeca-2,4,9-trien-1-ol,
3,7,10-trimethyldodeca-2,4,9-trien-1-ol,
3,6,10-trimethylundeca-2,4,9-trien-1-ol, Each of:

methyl 3,7,10,11-tetramethyldodeca-2,4,10-trienoate,
methyl 11-methoxy-3,7,11-trimethyldodeca-2,4-dienoate,
methyl 10-methoxy-2,7,10-trimethylundeca-2,4-dienoate,
methyl 3,5,7,11-tetramethyldodeca-2,4,10-trienoate,
methyl 3,4,7,11-tetramethyldodeca-2,4,10-trienoate,
methyl 3,5,7,10,11-pentamethyldodeca-2,4,10-trienoate,
methyl 11-ethoxy-3,7,11-trimethyldodeca-2,4-dienoate and
methyl 11-chloro-3,7,11-trimethyldodeca-2,4-dienoate is reduced using lithium aluminum hydride to the respective C-1 alcohol, i.e., 3,7,10,11-tetramethyldodeca-2,4,10-trien-1-ol,
11-methoxy-3,7,11-trimethyldodeca-2,4-dien-1-ol,
10-methoxy-3,7,10-trimethylundeca-2,4-dien-1-ol,
3,5,7,11-tetramethyldodeca-2,4,10trien-1-ol,
3,4,7,11-tetramethyldodeca-2,4,10-trien-1-ol,
3,5,7,10,11-pentamethyldodeca-2,4,10-trien-1-ol,
11-ethoxy-3,7,11-trimethyldodeca-2,4-dien-1-ol and
11-chloro-3,7,11-trimethyldodeca-2,4,-dien-1-ol.

EXAMPLE 50

To a mixture of 4 g. of 3,7,11-trimethyldodeca-2,4,10-trien-1-ol, and 25 ml. of benzene at 0° is added a solution of 5 ml. of phosphorus tribromide in 18 ml. of benzene over about 15 minutes. The mixture is stirred at 0° for 1 hour. The mixture is then poured onto ice and extracted with pentane. The organic phase is washed with aqueous sodium bicarbonate, water and then brine, dried over magnesium sulfate and evaporated to yield 1-bromo-3,7,11-trimethyldodeca-2,4,10-triene.

The process of this example is repeated using each of the alcohols of Example 49 to prepare the respective bromide, i.e., 3,7,11-trimethyltrideca-2,4,10-trienyl bromide,
3,11-dimethyl-7-ethyltrideca-2,4,10-trienyl bromide,
7,11-diethyl-3-methyltrideca-2,4,10-trienyl bromide,
3,8,12-trimethyltrideca-2,4,11-trienyl bromide,
3,7,10-trimethylundeca-2,4,9-trienyl bromide,
3,7,10-trimethyldodeca-2,4,9-trienyl bromide,
3,6,10-trimethylundeca-2,4,9-trienyl bromide,
3,7,10,11-tetramethyldodeca-2,4,10-trienyl bromide,
11-methoxy-3,7,11-trimethyldodeca-2,4-dienyl bromide,
10-methoxy-3,7,10-trimethylundeca-2,4-dienyl bromide,
3,6,7,11-tetramethyldodeca-2,4,10-trienyl bromide,
3,4,7,11-tetramethyldodeca-2,4,10-trienyl bromide,
3,5,7,10,11-pentamethyldodeca-2,4,10-trienyl bromide,
11-ethoxy-3,7,11-trimethyldodeca-2,4-dienyl bromide,
11-chloro-3,7,11-trimethyldodeca-2,4-dienyl bromide.

By repeating the process of this example using phosphorus trichloride in place of phosphorus tribromide, the novel allylic chlorides are prepared, i.e., 3,7,11-trimethyldodeca-2,4,10-trienyl chloride, 3,7,11-trimethyltrideca-2,4,10-trienyl chloride, 3,11-dimethyl-7-ethyltrideca-2,4,10-trienyl chloride, etc.

EXAMPLE 51

Ten grams of 1-bromo-3,7,11-trimethyldodeca-2,4,10-triene is mixed with 50 ml. of benzene, cooled to 5°–10° and saturated with ammonia. The resulting mixture is stirred for 4 hours allowing the temperature to rise to about 20° while maintaining dry conditions. The mixture is washed with dilute sodium hydroxide and then evaporated under reduced pressure to yield 3,7,11-trimethyldodeca-2,4,10-trienylamine.

By repeating the process of this example using the allylic bromides or chlorides of Example 50, the respective amines are prepared, e.g., 3,7,11-trimethyltrideca-2,4,10-trienylamine, 3,11-dimethyl-7-ethyltrideca-2,4,10-trienylamine, 11-methoxy-3,7,11-trimethyldodeca-2,4-dienylamine, 10-methoxy-3,7,10-trimethylundeca-2,4-dienylamine, 11-chloro-3,7,11-trimethyldodeca-2,4-dienylamine, etc.

EXAMPLE 52

Five grams of 1 bromo-3,7,11-trimethyldodeca-2,4,10-triene in 25 ml. of benzene is mixed with 4 g. of diethylamine and the mixture stirred for about three hours. Methylene chloride (50 ml.) is added and the mixture washed with dilute sodium hydroxide and then water and evaporated to yield N,N-diethyl 3,7,11-trimethyldodeca-2,4,10-trienylamine.

The process of this example is repeated using either the bromides or chlorides of Example 50 as the starting material to prepare the respective N,N-diethyl amine, e.g., N,N-diethyl 3,7,11-trimethyltrideca-2,4,10-trienylamine, N,N-diethyl 3,11-dimethyl-7-ethyl-trideca-2,4,10-trienylamine, N,N-diethyl 11-methoxy-3,7,11-trimethyldodeca-2,4-dienylamine, N,N-diethyl 10-methoxy-2,7,10-trimethylundeca-2,4-dienylamine, N,N-diethyl 11-chloro 3,7,11-trimethyldodeca-2,4-dienylamine, N,N-diethyl 3,7,10-trimethylundeca-2,4-dienyl amine, etc.

Other amines of the present invention of formula A and B are prepared by use of the foregoing procedure using an amine of the formula:

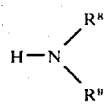

such as dimethylamine, ethylamine, methylamine, pyrrolidine, morpholine, 4-ethylpiperazine, and the like, in place of diethylamine. Thus, there is prepared N,N-dimethyl 3,7,11-trimethyldodeca-2,4,10-trienylamine, N,N-dimethyl 3,7,11-trimethyltrideca-2,4,10-trienylamine, N-ethyl 3,7,11-trimethyldodeca-2,4,10-trienylamine, N-ethyl 3,7,11-trimethyltrideca-2,4,10-trienylamine, etc.

Although not intending to be limited by a theoretical explanation, the effectiveness of the compounds of the present invention to control insects is attributed to the property of these novel compounds to mimic the activity of juvenile hormone. While the methods of applying and carriers for conventional insecticides are usually adaptable to the practical use of the compounds of the present invention, the mechanism of action of these novel compounds is unlike that of conventional insecticides. Whereas conventional insecticides are dependent upon direct knock-down effect, toxity effect or paralyzing effect, the compounds of this invention achieve control by reason of their ability to inhibit metamorphosis, inhibit reproduction due to abnormal development, break diapause at an unfavorable time, or as a direct insecticide, particularly at the embryo stage and larvae stage. Treatment of insects in accordance with the present invention can be achieved via ingestion of the active compound in the normal food of the insect and by topical application, that is — by contact of the epidermis of the insect as by spraying the insect and habitat of the insect or exposure to vapors of the active compound which penetrate into the insect.

The compounds of the present invention can be used in conjunction with other juvenile hormone active substances and conventional insecticides to obtain a broad spectrum of activity or to provide more immediate effect on very heterogeneous populations. Typical insecticides which may be combined with the compounds of the present invention are Malathion, Sevin, Vapona, Abate, synthetic and natural pyrethrins, and the like, and usually within the ratio of between 10:1 to 1:10, by weight.

EXAMPLE 53

To a solution of 6.2 g. of ethyl 11-methoxy-3,7,11-trimethyldodeca-2,4-dienoate in 80 ml. of dry ether is added 3.2 ml. of lithium aluminum hydride (3.9M) in ether slowly, at −78°, with stirring, under argon. The mixture is stirred for 2 hours at −78° and then warmed to about −50°. After 1 hour, the mixture is warmed slowly to about −10° over 4 hours. Then there is added 0.5 ml. of water, 0.5 ml. of 15% sodium hydroxide and 1.5 ml. of water. The mixture is then poured into water, washed with water and brine, dried over magnesium sulfate and evaporated to yield 11-methoxy-3,7,11-trimethyldodeca-2,4-dien-1-ol.

EXAMPLE 54

To a solution of 1.90 g. of 11-methoxy-3,7,11-trimethyldodeca-2,4-dien-1-ol in 20 ml. of ether is added a solution of 0.80 g. of phosphorus tribromide in 10 ml. of ether, under nitrogen, with stirring at −50°. The reaction mixture is stirred for three hours at −60° to −40° and then poured into ice water, which is then washed with sodium bicarbonate solution water and brine, dried over calcium sulfate and evaporated under reduced pressure to yield 11-methoxy-3,7,11-trimethyldodeca-2,4-dienyl bromide.

EXAMPLE 55

To 250 ml. of anhydrous pyridine, cooled in an ice-bath, is added 35.2 g. of p-toluenesulfonyl chloride. When the sulfonyl chloride is dissolved, 34 g. of 3,7,11-trimethyldodeca-2,4,10-trien-1-ol is added with 210 ml. of anhydrous pyridine. The reaction mixture is stirred at about 5°–10° for 24 hours. Then 40 ml. of cold water is added and the mixture stirred for one hour at ice temperature. The mixture is extracted with pentane. The pentane extracts are washed with 10% HCl and water, dried over potassium sulfate/potassium carbonate and concentrated under reduced pressure. The concentrate is taken up in 50 ml. of dry acetone and added to a solution of 36 g. of dry sodium iodide in 150 ml. of dry acetone. The reaction mixture is stirred at room temperature for about 20 hours and then filtered. The filtrate is concentrated and taken up in pentane. The pentane solution is washed with water, dried over sodium sulfate and evaporated to yield 3,7,11-trimethyldodeca-2,4,10-trienyl iodide, which can be purified by chromatography.

EXAMPLE 56

A mixture of 33 g. of 1-bromo-3,7,11-trimethyldodeca-2,4,10-triene and 100 ml. of dry ethylene glycol is slowly added with stirring, to a suspension of 11.5 g. of potassium fluoride in 30 ml. of dry ethylene glycol and heated to about 120°, under an inert atmosphere. When addition is completed, the reaction mixture is stirred for about an additional 16 hours while maintaining the temperature at 120°. Then the mixture is cooled and 200 ml. of ether added. The mixture is washed thoroughly with water and the ether phase dried over sodium sulfate and solvent evaporated under reduced pressure to yield 1-fluoro-3,7,11-trimethyldodeca-2,4,10-triene.

The same compound can be prepared by using an equivalent amount of silver fluoride in place of potassium fluoride.

EXAMPLE 57

Using the procedure of Example 55, each of
11-methoxy-3,7,11-trimethyldodeca-2,4-dien-1-ol,
11-ethoxy-3,7,11-trimethyldodeca-2,4,-dien-1-ol,
3,7,10-trimethylundeca-2,4,9-trien-1-ol,
10-methoxy-3,7,10-trimethylundeca-2,4-dien-1-ol,
11-methoxy-3,7,10,11-tetramethyldodeca-2,4,-dien-1-ol, and
3,7,10,11-tetramethyldodeca-2,4,10-trien-1-ol is converted into the iodide, that is
11-methoxy-3,7,11-trimethyldodeca-2,4-dienyl iodide,
11-ethoxy-3,7,11-trimethyldodeca-2,4-dienyl iodide,
3,7,10-trimethylundeca-2,4,9-trienyl iodide,
10-methoxy-3,7,10-trimethylundeca-2,4-dienyl iodide,
11-methoxy-3,7,10,11-tetramethyldodeca-2,4-dienyl iodide and
3,7,10,11-tetramethyldodeca-2,4,10-trienyl iodide.

EXAMPLE 58

By using the process of Example 56, each of
11-methoxy-3,7,11-trimethyldodeca-2,4-dienyl fluoride,
11-methoxy-3,7,10,11-tetramethyldodeca-2,4-dienyl fluoride,
10-methoxy-3,7,10-trimethylundeca-2,4-dienyl fluoride,
3,7,10,11-tetramethyldodeca-2,4,10-trienyl fluoride,
3,7,10-trimethylundeca-2,4,9-trienyl fluoride, and
3,7,11-trimethyltrideca-2,4,10-trienyl fluoride is prepared from the respective bromide precursor,
11-methoxy-3,7,11-trimethyldodeca-2,4-dienyl bromide,
11-methoxy-3,7,10,11-tetramethyldodeca-2,4-dienyl bromide,
10-methoxy-3,7,10-trimethylundeca-2,4-dienyl bromide,
3,7,10,11-tetramethyldodeca-2,4,10-trienyl bromide,
3,7,10-trimethylundeca-2,4,10-trienyl bromide, and
3,7,11-trimethyltrideca-2,4,10-trienyl bromide.

What is claimed is:

1. A compound selected from the following formula:

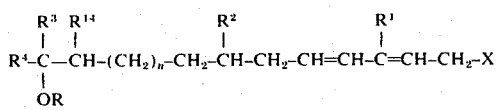

wherein,
 $n$ is zero or one;
 R is lower alkyl;
 each of $R^1$, $R^2$, $R^3$ and $R^4$ is methyl or ethyl; and
 X is bromo, chloro, fluoro or iodo.

2. A compound according to claim 1 wherein $n$ is one; $R^1$ is methyl; and R is lower alkyl of one to four carbon atoms.

3. A compound according to claim 2 wherein each of $R^2$ and $R^3$ is methyl.

4. A compound according to claim 3 wherein X is bromo or chloro and R is methyl or ethyl.

5. A compound according to claim 3 wherein X is bromo or chloro.

6. A compound according to claim 5 wherein each of R, $R^2$, $R^3$ and $R^4$ is methyl.

7. The compound, 11-methoxy-3,7,11-trimethyldodeca-2,4-dienyl bromide, according to claim 6.

8. The compound, 11-ethoxy-3,7,11-trimethyldodeca-2,4-dienyl bromide, according to claim 5.

9. The compound, 11-methoxy-3,7,11-trimethyldodeca-2,4-dienyl iodide, according to claim 3.

* * * * *